United States Patent [19]
Nakao et al.

[11] Patent Number: 5,190,542
[45] Date of Patent: Mar. 2, 1993

[54] SURGICAL RETRIEVAL ASSEMBLY AND RELATED METHOD

[76] Inventors: Naomi L. Nakao, 303 E. 57th St., New York, N.Y. 10022; Peter J. Wilk, 185 W. End Ave., New York, N.Y. 10023; John V. Mizzi, 30 Cramer Rd., R.F.D. #3, Poughkeepsie, N.Y. 12603

[21] Appl. No.: 892,214

[22] Filed: Jun. 2, 1992

Related U.S. Application Data

[63] Continuation-in-part of Ser. No. 788,035, Nov. 5, 1991.

[51] Int. Cl.$^5$ .............................................. A61B 17/36
[52] U.S. Cl. ........................................ 606/47; 606/1; 606/37; 606/39; 606/40; 606/45; 606/46; 606/48; 606/49; 606/50; 606/110; 606/113; 606/114
[58] Field of Search ............. 606/1, 32, 37, 39, 45–52, 606/110, 113, 114, 127, 128, 40

[56] References Cited

U.S. PATENT DOCUMENTS

| | | | |
|---|---|---|---|
| 3,715,829 | 2/1973 | Hamilton | 43/12 |
| 4,326,530 | 4/1982 | Fleury | 606/47 |
| 4,557,255 | 12/1985 | Goodman | 606/127 |
| 5,084,054 | 1/1992 | Bencini et al. | 606/127 |

Primary Examiner—Stephen C. Pellegrino
Assistant Examiner—Glenn Dawson
Attorney, Agent, or Firm—R. Neil Sudol; Henry D. Coleman

[57] ABSTRACT

A surgical instrument assembly for use in snare cauterization operations comprises a tubular sheath member, a metallic cauterization loop, and a metal wire operatively connected to the loop, the wire passing longitudinally through the sheath. An electrical supply is operatively connectable to the wire for feeding an electrical current to the loop via the wire, while a manually actuatable shifter is operatively connected to the wire for longitudinally sliding the wire along the sheath in alternately opposite directions. A flexible web member is connected to the loop to form a capture pocket, the loop defining a mouth opening of the pocket. During use of the snare cauterization instrument, the loop is at least partially expanded from a collapsed configuration and passed over a polyp to be removed, so that the web member substantially surrounds the selected polyp. The loop is then closed to engage the polyp around a base region thereof and an electrical current is subsequently conducted through the loop to burn through the polyp at the base region thereof. Severance of the polyp occurs upon a closure of the cauterization loop by its being withdrawn or retracted into the tubular sheath member. The severed polyp is automatically captured by the web member.

21 Claims, 7 Drawing Sheets

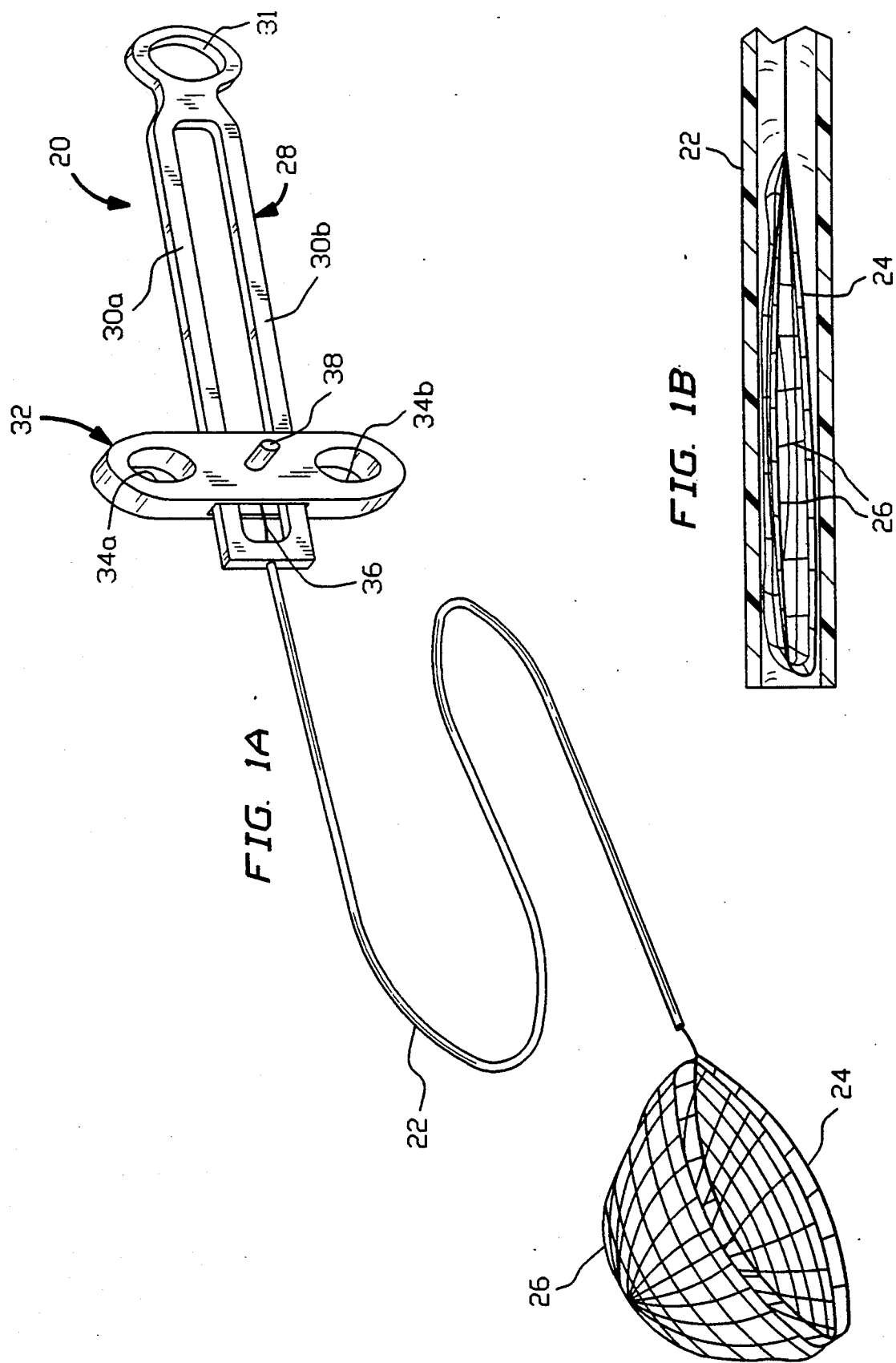

SURGICAL RETRIEVAL ASSEMBLY AND RELATED METHOD

CROSS-REFERENCE TO RELATED APPLICATION

This application is a continuation in part of commonly owned application Ser. No. 788,035 filed Nov. 5, 1991.

FIELD OF THE INVENTION

This invention relates to a surgical instrument assembly for use in retrieving objects from internal body cavities. This invention also relates, more specifically, to a surgical instrument assembly for use in snare cauterization operations. This invention also relates to a related method for retrieving objects from internal body cavities and more particularly to a method for capturing and/or retrieving polyps and other clumps of organic tissue which have been severed from a patient's internal organs via a snare cauterization technique.

BACKGROUND OF THE INVENTION

In a conventional snare operation, an endoscope is inserted into an internal cavity of a patient, e.g., into the colon, and is used to locate abnormal tissue growths such as polyps in the internal cavity. Upon the locating of a polyp or other growth which is to be removed, a wire extending through a tube in the biopsy channel of the endoscope is slid in the distal direction so that a cauterization loop connected to the wire is ejected from the distal end of the tube and the endoscope. The loop and the endoscope are manipulated from outside of the patient to pass the loop over the polyp or growth. The wire is then withdrawn in the proximal direction to tighten the loop around a base region or neck of the polyp. Once the loop is in contact with the base region of the polyp, an electrical current is conducted through the loop via the wire. Generally, as the loop is closed about the base region of the polyp, electrical current is transmitted through the narrowed organic tissues and thereby generates therein heat sufficiently great to cut and cauterize.

Once a polyp is severed by such a snare cauterization technique, it frequently becomes difficult to capture the polyp and retrieve it from the patient. Sometimes the cauterization loop is used in an effort to ensnare the polyp. Other capture techniques involve the use of forceps or the application of suction. In using forceps, the snare cauterization tube is removed from the biopsy channel of the endoscope and replaced with the forceps. In using suction, a vacuum is applied via a suction channel of the endoscope.

No matter which specific technique is used, the polyp frequently escapes from the capturing instrumentality and falls away into the colon (or other cavity). Especially in cases where the polyp is large, the effort and time expended in retrieving the severed polyp may rival or even exceed the effort and time required to locate and sever the polyp. In extreme cases, the endoscope must be removed without the polyp and the patient given an enema in an attempt to flush out the polyp from the colon.

Furthermore, there are numerous cases where a severed polyp is never recovered. Sometimes, the polyp is masserated during the retrieval attempt. In all such cases, the pathologist is unable to determine whether the polyp contains carcinoma in situ (localized) or infiltrative carcinoma (spread). The patient must then undergo a colon ressection, sometimes unnecessarily.

In any event, the manipulations necessary to remove a severed polyp generally increase the trauma to the patient, the expense of the surgery and the hospitalization time. There is now a long-felt need to improve the snare cauterization technique to facilitate the capture and retrieval of severed polyps.

OBJECTS OF THE INVENTION

An object of the present invention is to provide an improved method for the removal of portions of internal body organs or other objects from patients.

A more specific object of the present invention is to provide an improved method for the performance of snare cauterization.

Another object of the present invention is to provide a snare cauterization technique wherein the capture and retrieval of severed polyps is facilitated.

Another, more particular, object of the present invention is to provide a snare cauterization technique wherein trauma to the patient and time in surgery are reduced.

A further object of the present invention is to provide an instrument assembly for use in removing portions of body organs or other objects from patients.

Yet another, more particular, object of the present invention is to provide such an instrument assembly which facilitates the capture and retrieval of severed polyps and other clumps of severed body tissues from the internal cavities of patients.

Another particular object of the present invention is to provide such an instrument assembly which is simple to manufacture and therefore inexpensive.

A further particular object of the present invention is to provide such an instrument assembly which is easy to use.

An additional particular object of the present invention is to provide such an instrument assembly which is disposable. Such an instrument assembly requires no lengthy sterilization procedure and reduces the spread of infectitous diseases such as AIDS.

These and other objects will be apparent from the following descriptions.

SUMMARY OF THE INVENTION

A surgical instrument assembly for use in snare cauterization operations comprises, in accordance with the present invention, a flexible cauterization loop, an electrical conductor operatively connected to the cauterization loop for feeding an electrical current thereto, and a flexible auxiliary loop connected to the cauterization loop at most at three points. An actuator is operatively connected to the cauterization loop and the auxiliary loop for alternately expanding and contracting the cauterization loop and the auxiliary loop. In addition, a flexible web member is connected to the auxiliary loop essentially around a circumference thereof to form a capture pocket, the auxiliary loop defining a mouth opening of the pocket.

The actuator may include a finger ring or knob at a proximal end of the instrument assembly for sliding the cauterization loop and the auxiliary loop alternately into and out of the distal end of a tubular sheath member.

Preferably, the cauterization loop is made of a metallic material while the auxiliary loop is fashioned of a synthetic resin or polymeric material.

Pursuant to another feature of the present invention, the cauterization loop and the auxiliary loop are disposed in parallel planes and are contiguous or proximate to one another. The cauterization loop and the auxiliary loop may be disposed in essentially the same plane. Preferably, the auxiliary loop is larger than the cauterization loop. Thus, the auxiliary loop is spaced, if only slightly, from the cauterization loop and does not interfere with the cutting and cauterization operations.

In one specific embodiment of the present invention, the flexible web member is a net which is fixed to the auxiliary loop at only two points, at the distal end of the loop and at the proximal end thereof, inside the housing tube. The remaining connections of the net to the auxiliary loop are slidable, thereby facilitating an opening and closing of the net while ensuring that the net does not bunch or collapse at one end of the auxiliary loop or the other.

According to a specific embodiment of the present invention, the auxiliary loop is connected to the cauterization loop only at a distal end thereof. More particularly, the cauterization loop may be provided at the distal end with a distally projecting extension to which the auxiliary loop is connected.

Where the auxiliary loop is connected to the cauterization loop only at a distal end thereof, the proximal end of the auxiliary loop, like the cauterization loop, is connected to an actuator (such as a push-pull ring or knob) at the proximal end of the instrument assembly. Thus, both the cauterization loop and the auxiliary loop are controlled, i.e., alternately expanded and contracted, by manipulations at the proximal end of the instrument assembly.

Alternatively, the auxiliary loop is connected to the cauterization loop only at a distal end and a proximal end of the cauterization loop. At the proximal end, the auxiliary loop and the cauterization loop may be connected to one another at one or two points.

The assembly may further comprise a tubular sheath member, the electrical conductor and at least a portion of the actuator extending through the sheath member.

Pursuant to another basic conceptualization of the present invention, a surgical instrument assembly for use in snare cauterization operations comprises a flexible cauterization loop, an electrical conductor operatively connected to the cauterization loop for feeding an electrical current thereto, and a flexible auxiliary loop larger than the cauterization loop and connected thereto. An actuator is operatively connected to the cauterization loop and the auxiliary loop for alternately expanding and contracting the cauterization loop and the auxiliary loop. A flexible web member is connected to the auxiliary loop essentially around a circumference thereof to form a capture pocket, the auxiliary loop defining a mouth opening of the pocket. As discussed hereinabove with reference to a preferred embodiment of the invention, the flexible web member is a net which is fixed to the auxiliary loop at only two points, at the distal end of the loop and at the proximal end thereof, inside the housing tube. The remaining connections of the net to the auxiliary loop are slidable, to make a larger or smaller mouth opening, as needed. At the onset of a cauterization procedure, the mouth opening is large to envelope the polyp. Subsequently, the mouth opening is small or essentially nonexistent, as the cauterization and auxiliary loops are drawn into the distal end of the tubular sheath to sever and capture the polyp. It is to be noted that the loops are not drawn so far into the tubular sheath member as to masserate the polyp. Instead, the polyp remains outside the sheath member and outside the endoscope during the withdrawal thereof from the patient.

A method for removing a selected portion of internal body tissues of a patient comprises, in accordance with the present invention, the steps of (a) providing a conductive cauterization loop to which an auxiliary loop is connected, a flexible web member being connected to the auxiliary loop essentially along a circumference thereof to define an expandable pocket, and (b) at least partially expanding the cauterization loop and the auxiliary loop from a collapsed configuration to an expanded configuration, wherein the auxiliary loop is larger than the cauterization loop and essentially parallel thereto. Further steps include (c) at least partially opening the web during the step of expanding, (d) passing the expanded loops over the selected internal body tissues to be removed, so that the web member substantially surrounds the selected internal body tissues, (e) partially closing the cauterization loop to engage the selected internal body tissues around a base region thereof while maintaining the web member surrounding the selected internal body tissues, and (f) conducting an electrical current through the cauterization loop to burn through the selected internal body tissues at the base region, thereby severing the selected internal body tissues at the base region. Upon a completed burning of the cauterization loop through the base region, the auxiliary loop is at least partially closed, thereby capturing the severed internal body tissues in the web member.

The present invention provides an improved method for the removal of portions of internal body organs from patients via snare cauterization.

In a method in accordance with the present invention, the capture and retrieval of severed polyps is facilitated. An instrument assembly in accordance with the present invention is simple to use. Accordingly, trauma to the patient and time in surgery are reduced. More specifically, time under anaesthesia with the accompanying side effects is reduced. Concomitantly, the expense of hospitalization is decreased.

BRIEF DESCRIPTION OF THE DRAWING

FIG. 1A is a schematic perspective view of a snare cauterization instrument assembly, showing a cauterization loop in an ejected, use configuration.

FIG. 1B is a schematic longitudinal cross-sectional view of a distal end of the cauterization instrument assembly of FIG. 1A, showing the cauterization loop in a withdrawn or retracted storage configuration inside the distal end of a tubular member of the instrument assembly.

DETAILED DESCRIPTION

Figure 2A:
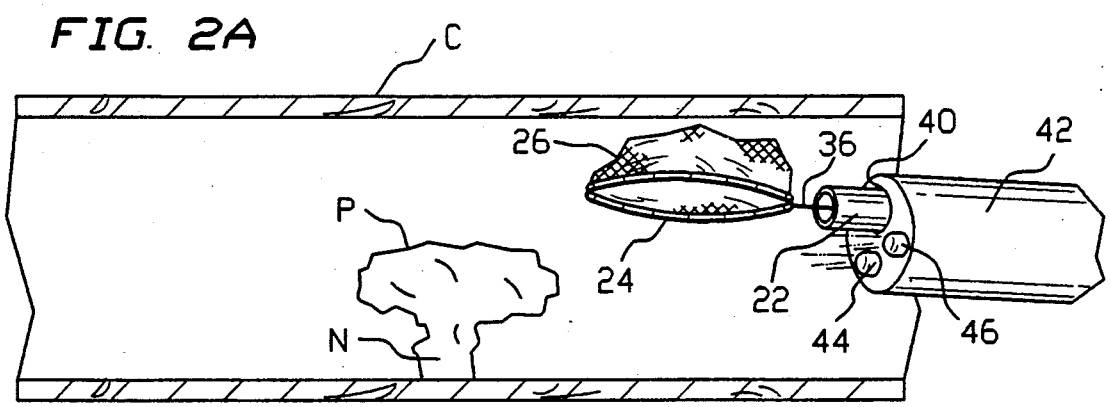
FIG. 2A is a schematic partial cross sectional view of a patient's colon with a polyp, showing the snare cauterization instrument assembly of FIG. 1A inserted in the biopsy channel of an endoscope which is itself inserted into the patient's colon, and further showing the instrument assembly in an initial stage of a snare cauterization procedure.

As illustrated in FIG. 1A, a snare cauterization instrument assembly comprises a hand held control module 20, a flexible tubular member 22 connected to a distal end of the control module, and an alternately expandable and closable cauterization loop 24 at the distal tip of the flexible tubular member 22. A flexible sheet or web 26 specifically in the form of a net is attached to cauterization loop 24 for defining a capture pocket. Loop 24 defines the mouth of the capture pocket.

Control module 20 comprises a body member or frame 28 which includes a pair of parallel rails 30a and 30b to which a slider member 32 is reciprocatably secured. Frame 28 has a thumb hole 31 at a proximal end, whereas slider member 32 has a pair of finger holes 34a and 34b and is fastened to the proximal end of a wire 36 which passes through tubular member 22 and is in turn connected to cauterization loop 24 at the distal end of tubular member 22 Wire 36 is sufficently flexible to bend with tubular member 22 during the negotiation thereby of curves or bends in a colon during surgery.

Slider member 32 is also provided with an electrical connector 38 which is couplable to a source of electrical energy. During a severing step of a cauterization operation, described in detail hereinafter with reference to FIG. 2E, electrical energy is fed to loop 24 via connector 38 and wire 36.

Capture web 26 is thin and flexible and preferably made of biologically inert flexible transparent synthetic resin or polymeric material such as polyethylene or nylon. Prior to the beginning of a snare cauterization operation, web 26 is disposed in a closed, folded or contracted state, together with loop 24, in the distal end of tubular member 22, as illustrated in FIG. 1B. Concomitantly, slider member 32 is retracted to the proximal end of rails 30a and 30b (towards the right side of frame 28 in FIG. 1A). Tubular member 22 is inserted in a biopsy channel 40 of an endoscope 42, as shown in FIG. 2A, and the endoscope is inserted into a body cavity of a patient, such as a colon C.

As illustrated further in FIG. 2A, endoscope 42 is conventionally provided at its distal end with a pair of apertures 44 and 46 for respectively delivering light to and receiving light from a surgical site.

Upon the discovery of a polyp P within colon C via the use of endoscope 42, the snare cauterization instrument assembly is shifted in a distal direction so that tubular member 22 protrudes from the distal end of biopsy channel 40. Then, slider member 32 is shifted in a distal direction to eject loop 24 and capture web 26 from tubular member 22. Upon ejection, loop 24 and capture web 26 expand from a contracted or closed configuration into an at least partially opened configuration, as shown in FIG. 2A.

Figure 2B:
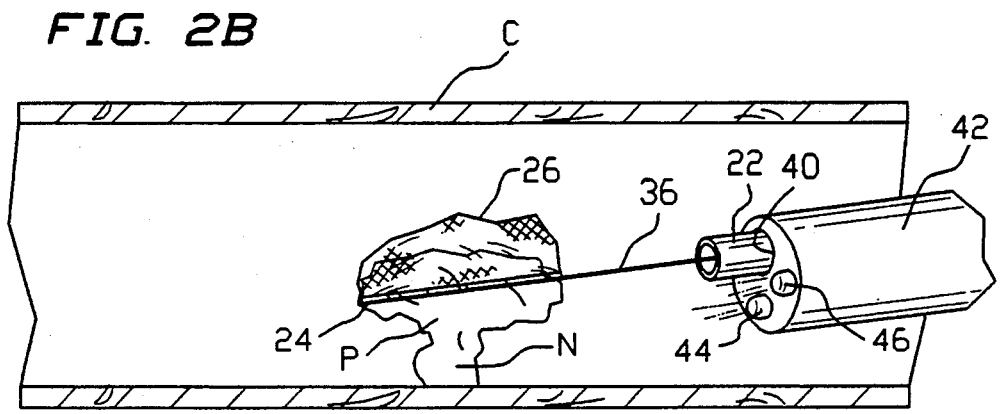
FIG. 2B is a schematic partial cross sectional view similar to FIG. 2A, showing a loop of the snare cauterization instrument assembly of FIG. 1A being passed around the polyp of FIG. 2A.
Figure 2C:
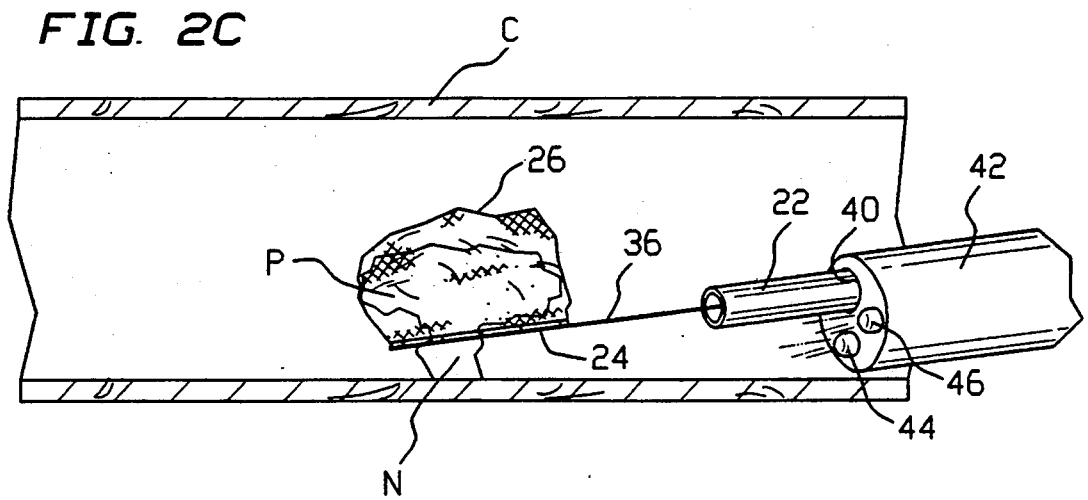
FIG. 2C is a schematic partial cross sectional view similar to FIGS. 2A–2B, showing the loop of the snare cauterization instrument assembly of FIG. 1A completely passed around the polyp of FIG. 2A.

FIG. 2B depicts a later stage in the cauterization procedure. The snare cauterization instrument assembly of FIG. 1A is manipulated to pass loop 24 around polyp P, with capture web 26 following. Eventually, loop 24 encircles a base region or neck N of polyp P and the polyp is surrounded by capture web 26, as shown in FIG. 2C.

Figure 2D:
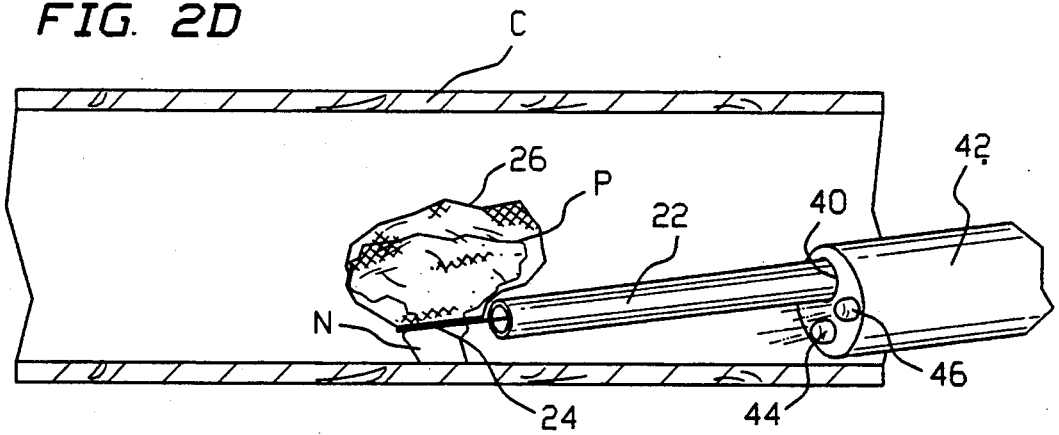
FIG. 2D is a schematic partial cross sectional view similar to FIGS. 2A–2C, showing the loop of the snare cauterization instrument assembly of FIG. 1A being tightened around a base or neck of the polyp.

At that juncture, slider member 32 is pulled back in the proximal direction, whereby wire 36 pulls loop 24 partially back into the distal end of tubular member 22, thereby causing loop 24 to tighten about neck N of polyp P, as illustrated in FIG. 2D.

Figure 2E:
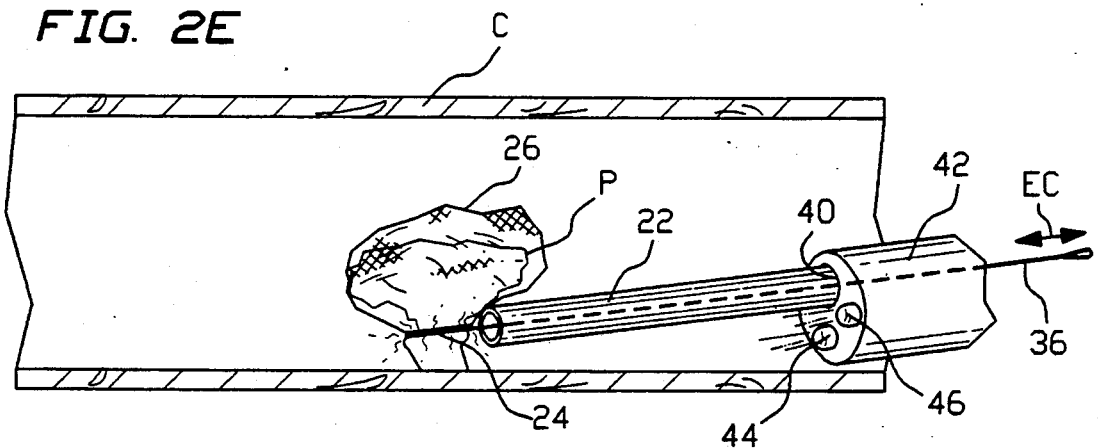
FIG. 2E is a schematic partial cross sectional view similar to FIGS. 2A–2D, showing the loop of the snare cauterization instrument assembly of FIG. 1A in an electrically energized state for burning through the base or neck of the polyp.
Figure 2F:
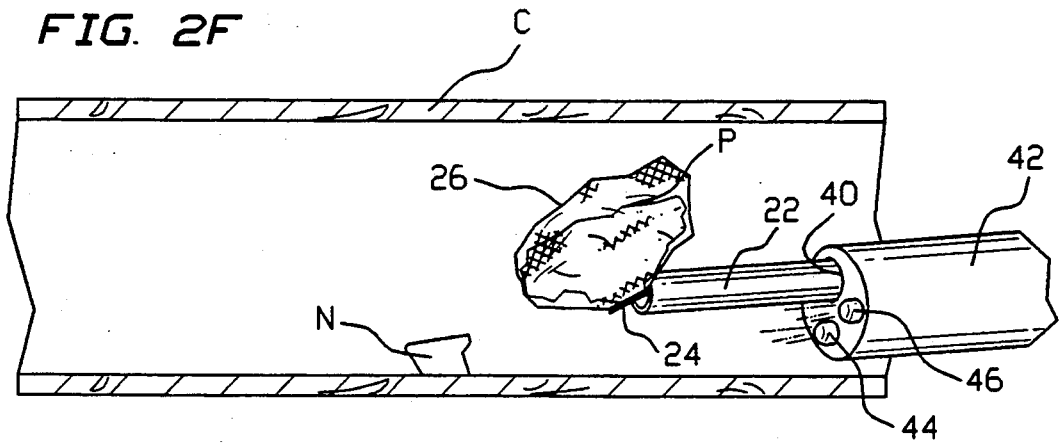
FIG. 2F is a schematic partial cross sectional view similar to FIGS. 2A–2E, showing the polyp severed from the colon wall and captured with the snare cauterization instrument assembly of FIG. 1A.
Figure 2G:
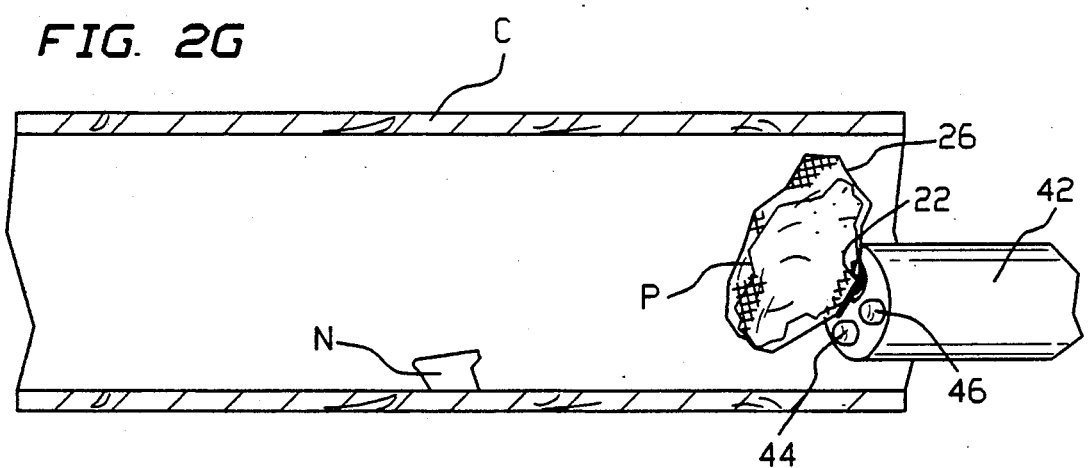
FIG. 2G is a schematic partial cross sectional view similar to FIGS. 2A–2G, showing the snare cauterization instrument assembly of FIG. 1A together with the captured polyp drawn towards the distal end of the endoscope.

As indicated in FIG. 2E, electrical current EC is then caused to pass through wire 36 and loop 24. Generally, electric currect from loop 24 is conducted through neck N of polyp P, thereby generating in the polyp tissues heat sufficiently great to sever and cauterize neck N. Upon the severing of polyp P at neck N, slider member 32 is pulled farther in the proximal direction, thereby pulling loop 24 further into the distal end of tubular member 22, as shown in FIG. 2F, to essentially close the loop. Polyp P is now securely trapped in capture web 26. In a further step, depicted in FIG. 2G, the entire snare cauterization instrument assembly including, in particular, tubular member 22, is shifted in the proximal direction relative to endoscope 42. However, care is taken not to draw the distal end of tubular member 22 and particularly capture web 26 with polyp P back into biopsy channel 40 of the endoscope. Polyp P remains in web or capture pocket 26 outside of tubular member 22 and endoscope 42 during the withrdawal of endoscope 42 from the patient.

Every polyp severed by a snare cauterization instrument as described and illustrated herein is captured immediately. Thus, the time for the capture and retrieval of severed polyps is reduced to a minimum. Trauma to patient is likewise reduced, as are hospitalization expenses.

Figure 3:
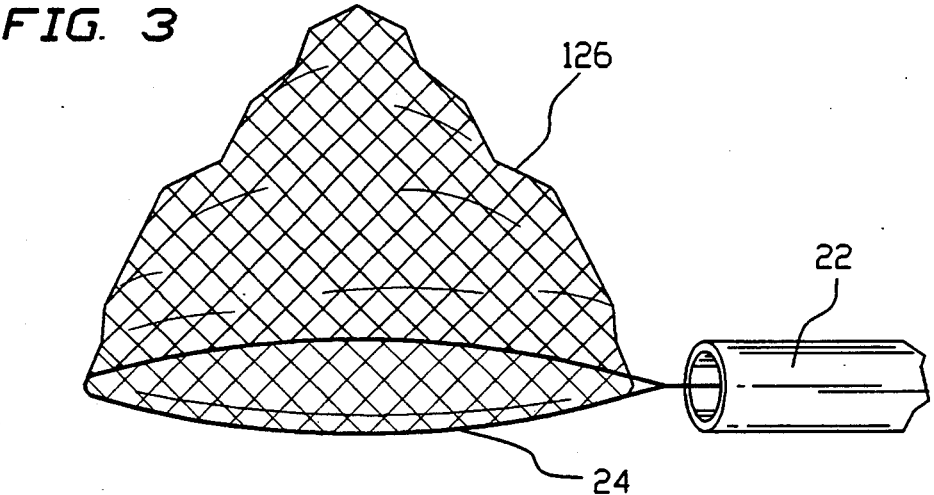
FIGS. 3–6 are schematic partial side perspective views, showing different specific embodiments of a snare cauterization instrument assembly.
Figure 4:
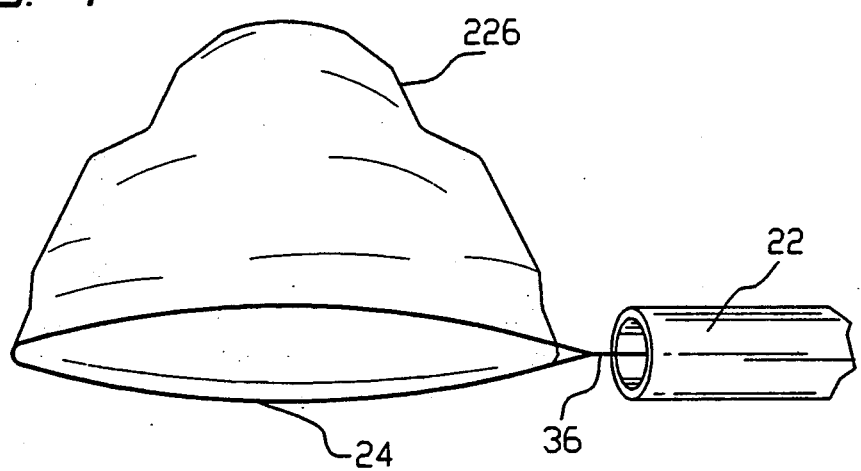
Figure 5:
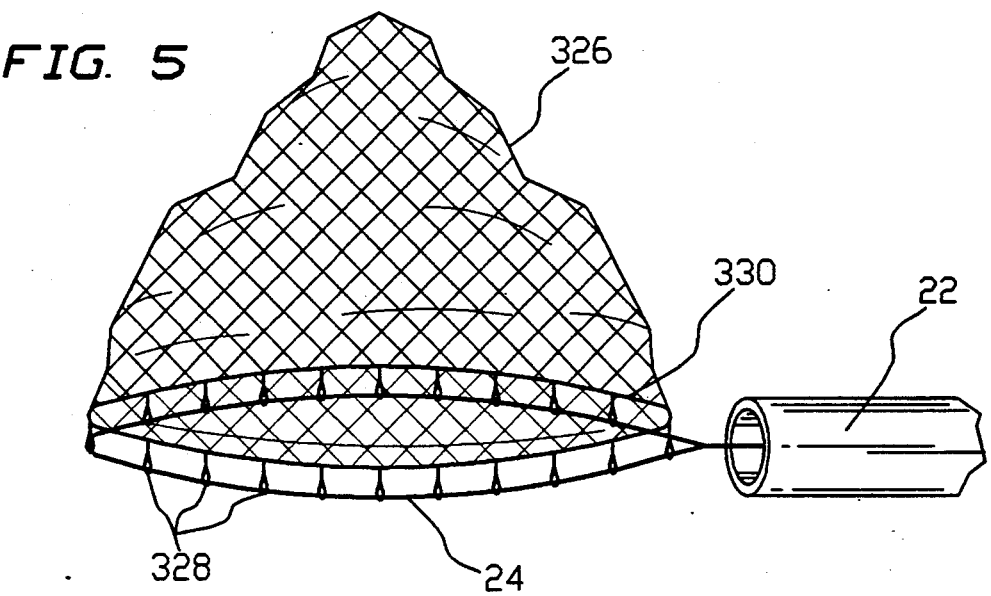
Figure 6:
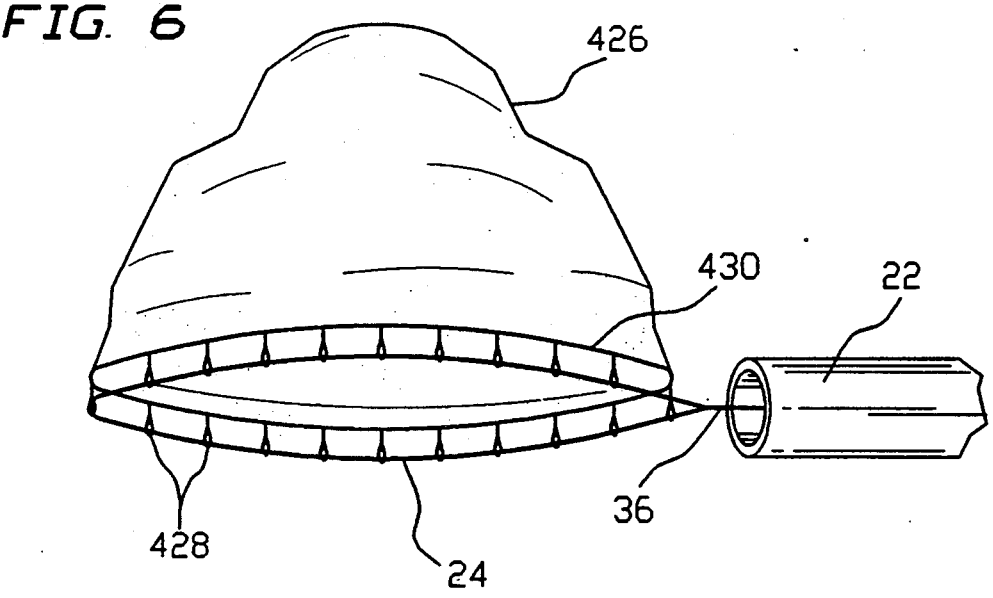

In FIGS. 3-6, like structural components bear the same reference designations. FIG. 3 shows a capture web 126 in the form of a net fastened directly to loop 24, while FIG. 4 shows a capture web 226 in the form of a continuous or solid transparent film fastened directly to loop 24. FIG. 5 illustrates a capture web 326 in the form of a net attached to loop 24 via a multiplicity of spaced ringlets 328. Loop 24 passes through ringlets 328, which are connected to a ring-shaped rim element 330 of web 326. Ringlets 328 are preferably made of a metallic material to facilitate the transmission of electrical current from cauterization loop 24 to the tissues of a polyp. FIG. 6 shows a capture web 426 in the form of a continuous or solid film of transparent polymeric material attached to loop 24 via a multiplicity of spaced ringlets 428. Loop 24 passes through ringlets 428, which are connected to a ring-shaped rim element 430 of web 326.

Figure 7:
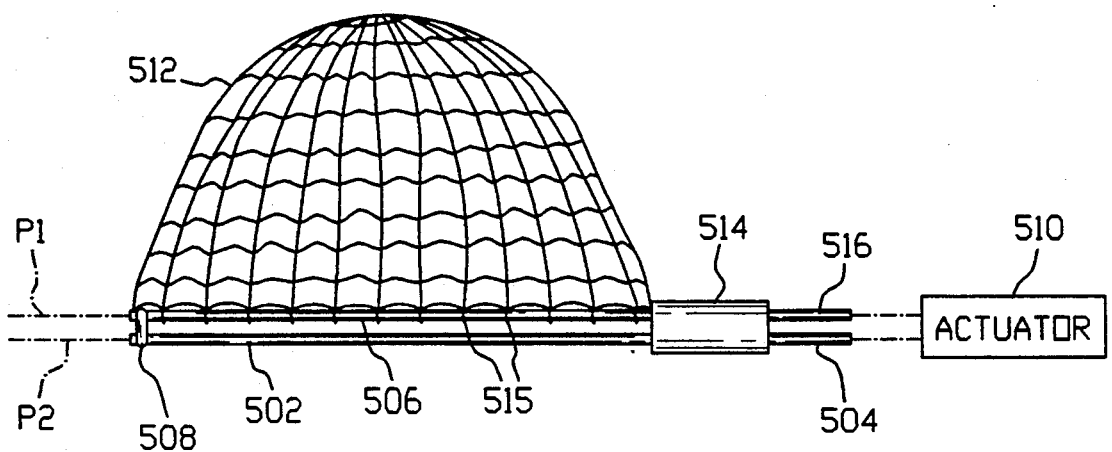
FIG. 7 is a schematic side elevational view, on an enlarged scale, of another embodiment of a snare cauterization instrument assembly, in accordance with the present invention, showing a pocket-defining web member on an auxiliary loop.

As illustrated in FIG. 7, a snare cauterization instrument assembly comprises a flexible cauterization loop 502, an electrical conductor 504 operatively connected to the cauterization loop for feeding an electrical current thereto, and a flexible auxiliary loop 506 connected via a fastening element 508 to the cauterization loop only at a distal end thereof. An actuator 510 is operatively connected to cauterization loop 502 and auxiliary loop 506 for alternately expanding and contracting the two loops in tandem with one another. A flexible web member 512 in the form of a net (or a continuous transparent membrane) is connected to auxiliary loop 506 essentially around the circumference thereof to form a capture pocket, auxiliary loop 506 defining a mouth opening of the pocket. Preferably, net 512 is fixed to auxiliary loop 506 only at a distal end and a proximal end (inside a tubular sheath member 514) thereof, the remaining connections 515 being slidable.

Actuator 510 is connected to cauterization loop 502 via conductor 504, which functions in response to manipulations of actuator 510 to eject cauterization loop 502 from a collapsed storage position inside the distal end of tubular sheath member 514 and subsequently to pull cauterization loop back into the sheath member. Actuator 510 is coupled to auxiliary loop 506 via a flexible wire or rod member 516 which like conductor 504 extends longitudinally through sheath member 514.

Figure 8:
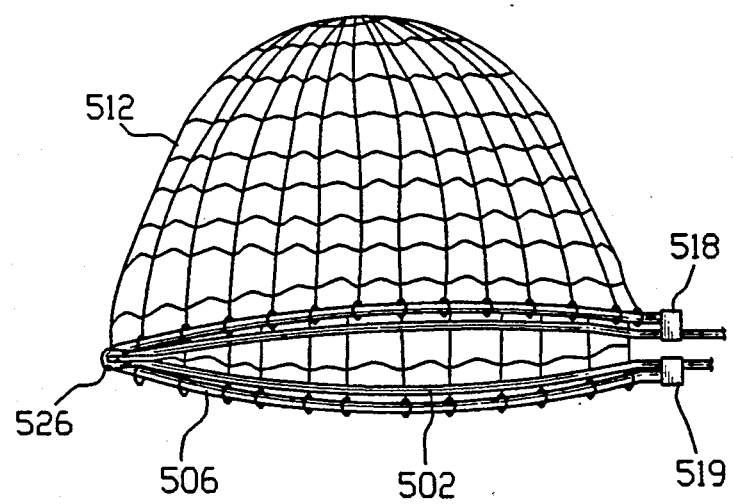
FIG. 8 is a schematic perspectie view, also on an enlarged scale, of a modified snare cauterization instrument assembly in accordance with the present invention, showing an auxiliary loop attached at three points to a cauterization loop.

Cauterization loop 502 and auxiliary loop 506 are disposed in parallel planes P1 and P2, respectively. As depicted in FIG. 8, auxiliary loop 506 may be connected at a proximal end to cauterization loop 502 at two points 518 and 519, as well as to the distal end of the cauterization loop. In that event, wire or rod member 516 may be omitted. As further shown in FIG. 8, auxiliary loop 506 is slightly larger than cauterization loop 502. The loops 502 and 506 are close, almost touching one another. As described above with reference to FIG. 7, web member 512 is fixedly connected to auxiliary loop 506 at a distal end and a proximal end thereof and slidably connected to the auxiliary loop between those ends.

Figure 9:
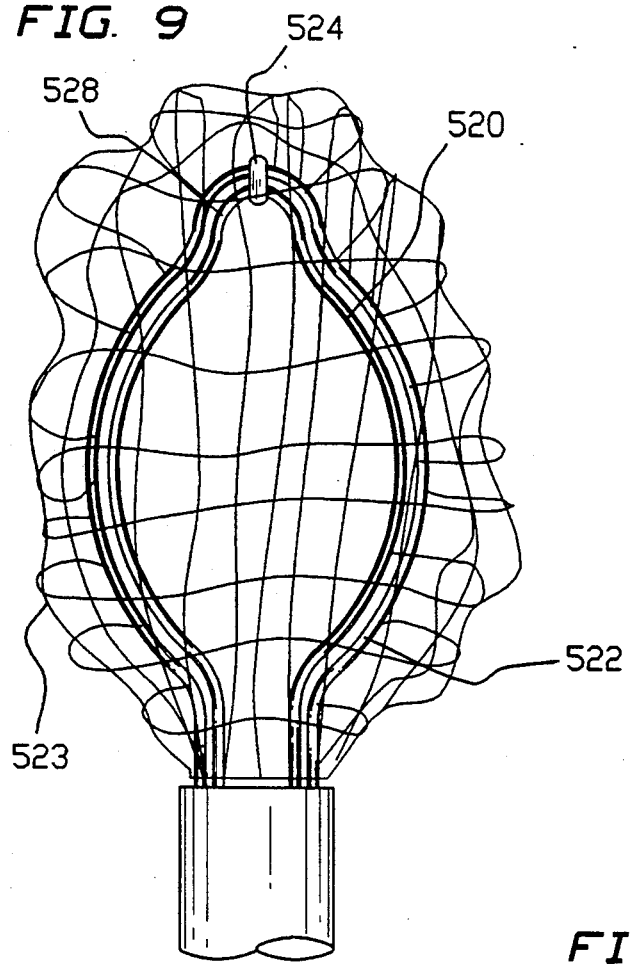
FIG. 9 is a schematic top view of another modified snare cauterization instrument assembly in accordance with the present invention, showing an auxiliary loop attached at one point to a cauterization loop.

FIG. 9 shows a cauterization loop 520 and an auxiliary loop 522 connected to one another at a distal end via a fastener 524. Cauterization loop 520 and auxiliary loop 522 are essentially coplanar in the expanded configuration illustrated in FIG. 9. During an ejection stroke and a subsequent retraction stroke of cauterization loop 520 and auxiliary loop 522 in response to the manipulations of an actuator (not shown) at a proximal end (not shown) of the instrument assembly, cauterization loop 520 and auxiliary loop 522 expand and contract in unison in essentially a common plane.

The embodiments of a cauterization snare instrument assembly illustrated in FIGS. 7-9 are less expensive to manufacture than the ringlet embodiments of FIG. 5 and 6 and enable use of a wider range of materials for the pocket or web member (512 in FIG. 7) than the embodiments of FIGS. 3 and 4. In addition, a primary advantage of the particular dual loop embodiments of FIGS. 7-9 is that auxiliary loops 506 and 522 are not connected to the cauterization loops 502 and 520 along operative portions thereof, thereby eliminating any possible interference that the auxiliary loops or capture nets 512 and 523 (FIG. 9) might otherwise exhibit with respect to the cutting and cauterization operations.

As illustrated in FIGS. 8 and 9, this elimination of possible interference in the cutting and cauterization operations is furthered by forming cauterization loops 502 and 520 at their distal ends with respective tongue-like extensions 526 and 528 to which auxiliary loops 506 and 522 are connected. Extensions 526 and 528 may be coated with an insulating material (not illustrated) and serve to separate fasteners 508 and 524 from the site of the cauterization procedure.

Auxiliary loops 506 and 522 are made of electrically nonconductive material preferably in the form of a synthetic resin or polymeric material such as polythylene or nylon.

In using the snare cauterization instrument assemblies of FIGS. 7-9, cauterization loop 502 or 520 and auxiliary loop 506 or 522 are expanded from a collapsed configuration inside the distal end of sheath member 514 to an expanded configuration. In the expanded configuration, auxiliary loop 506 or 522 is preferably larger than cauterization loop 502 or 520 and essentially parallel thereto. A special case of parallelism is found where the cauterization loop and the auxiliary loop are coplanar.

Pursuant to additional steps in the procedure, pocket or web member 512 is opened during the expansion of cauterization loop 502 or 520 and auxiliary loop 506 or 522 and the expanded loops are passed over a selected polyp or other internal tissue agglomeration to be removed, so that web member 512 substantially surrounds the polyp. Cauterization loop 502 or 520 is then closed by pulling it into the distal end of sheath member 514 or 528 (FIG. 9). The closure of cauterization loop 502 or 506 around a base region of the polyp while the cauterization loop is energized with electrical current serves to severe the polyp at its base. Maintaining web member 512 surrounding the polyp during the cauterization procedure serves to capture the severed polyp at the instant of its severance.

Figure 10:
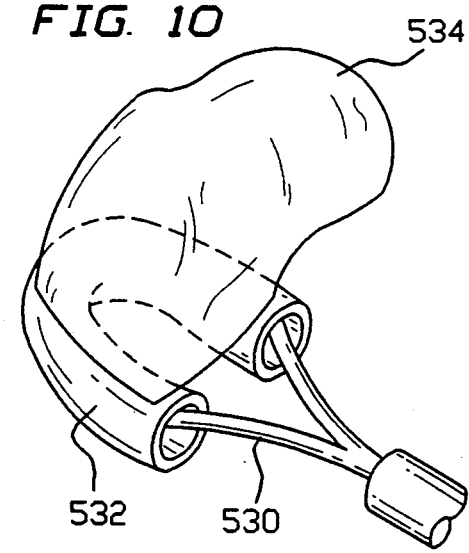
FIG. 10 is a schematic partial perspective view, on an enlarged scale, of an additional snare cauterization instrument assembly in accordance with the present invention.

As illustrated in FIG. 10, a modified snare cauterization assembly includes a cauterization loop 530 surrounded along a substantial portion of its length by a tubular jacket or sleeve 32 to which a flexible pocket-defining web member 534 is connected.

Figure 11:
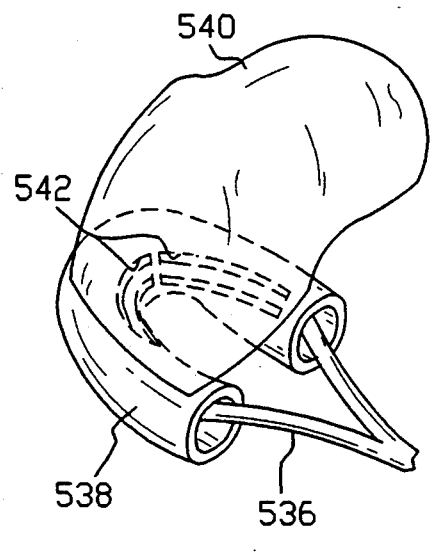
FIG. 11 is a schematic partial perspective view, on an enlarged scale, of yet a further snare cauterization instrument assembly in accordance with the present invention.

As illustrated in FIG. 11, another modified snare cauterization assembly comprises a cauterization loop 536 enclosed along essentially its entire length by a tubular jacket or sleeve 538 to which a flexible pocket-defining web member 540 is coupled. Sleeve 538 is provided along an inner side with a plurality of longitudinally extending windows 542 for facilitating or enabling the conduction of heat and/or electrical current from cauterization loop 536 to organic tissues of a polyp or other cell mass to be removed from a patient's body.

A cauterization instrument assembly as described herein is preferably disposable.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

WHAT IS CLAIMED IS:

1. A surgical instrument assembly for use in snare cauterization operations, comprising:
    a flexible cauterization loop;
    electrical conductor means operatively connected to said cauterization loop for feeding an electrical current thereto;
    a flexible auxiliary loop connected to said cauterization loop at most at three points;
    actuator means operatively connected to said cauterization loop and said auxiliary loop for alternately expanding and contracting said cauterization loop and said auxiliary loop; and
    a flexible web member connected to said auxiliary loop essentially around a circumference thereof to form a capture pocket, said auxiliary loop defining a mouth opening of said pocket.

2. The assembly defined in claim 1 wherein said cauterization loop and said auxiliary loop are disposed in parallel planes, proximately to one another, and are movable in unison.

3. The assembly defined in claim 2 wherein said auxiliary loop is larger than said cauterization loop.

4. The assembly defined in claim 1 wherein said auxiliary loop is connected to said cauterization loop only at a distal end thereof.

5. The assembly defined in claim 4 wherein said cauterization loop is provided at said distal end with a distally projecting extension, said auxiliary loop being connected to said cauterization loop at said extension.

6. The assembly defined in claim 1 wherein said auxiliary loop is connected to said cauterization loop only at a distal end and a proximal end of said cauterization loop.

7. The assembly defined in claim 1 wherein said auxiliary loop is made of electrically nonconductive material.

8. The assembly defined in claim 1, further comprising a tubular sheath member, said electrical conductor means and at least a portion of said actuator means extending through said sheath member.

9. The assembly defined in claim 1 wherein said web member is fixedly connected to said auxiliary loop at a pair of spaced points, said web member being slidably connected to said loop between said spaced points.

10. A surgical instrument assembly for use in snare cauterization operations, comprising:
    a flexible cauterization loop having an inner diameter in a fully opened configuration;
    electrical conductor means operatively connected to said cauterization loop for feeding an electrical current thereto;
    a flexible auxiliary loop connected to said cauterization loop, said auxiliary loop having an inner diameter in a fully opened configuration, said inner diameter of said auxiliary loop being larger than said inner diameter of said cauterization loop thus spacing said auxiliary loop from said cauterization loop so as not to interfere with cutting and cauterization operations;
    actuator means operatively connected to said cauterization loop and said auxiliary loop for alternately expanding and contracting said cauterization loop and said auxiliary loop; and
    a flexible web member connected to said auxiliary loop essentially around a circumference thereof to form a capture pocket, said auxiliary loop defining a mouth opening of said pocket.

11. The assembly defined in claim 10 wherein said cauterization loop and said auxiliary loop are disposed in parallel planes, proximately to one another, and are movable in unison.

12. The assembly defined in claim 10 wherein said cauterization loop and said auxiliary loop are disposed in essentially the same plane.

13. The assembly defined in claim 10 wherein said auxiliary loop is connected to said cauterization loop only at a distal end thereof.

14. The assembly defined in claim 13 wherein said cauterization loop is provided at said distal end with a distally projecting extension, said auxiliary loop being connected to said cauterization loop at said extension.

15. The assembly defined in claim 10 wherein said auxiliary loop is connected to said cauterization loop only at a distal end and a proximal end of said cauterization loop.

16. The assembly defined in claim 10 wherein said auxiliary loop is made of electrically nonconductive material.

17. The assembly defined in claim 10, further comprising a tubular sheath member, said electrical conductor means and at least a portion of said actuator means extending through said sheath member.

18. The assembly defined in claim 10 wherein said web member is made of a transparent material.

19. A surgical instrument assembly for use in snare cauterization operations, comprising:
    a flexible cauterization loop having an operative portion which is adapted to come into contact with tissues to be severed and cauterized, said cauterization loop including at least one portion which is adapted to be spaced from such tissues during a cauterization procedure;
    electrical conductor means operatively connected to said cauterization loop for feeding an electrical current thereto;
    a flexible auxiliary loop connected to said cauterization loop only at a plurality of spaced points, including said one portion, all spaced from said operative portion;
    actuator means operatively connected to said cauterization loop and said auxiliary loop for alternately expanding and contracting said cauterization loop and said auxiliary loop; and
    a flexible web member connected to said auxiliary loop essentially around a circumference thereof to form a capture pocket, said auxiliary loop defining a mouth opening of said pocket.

20. The assembly defined in claim 19 wherein said one portion is a tongue-like extension connected to said operative portion, said auxiliary loop being connected to said cauterization loop at said extension.

21. A method for removing a selected portion of internal body tissues of a patient, comprising the steps of:

providing a conductive cauterization loop to which an auxiliary loop is connected, a flexible web member being connected to said auxiliary loop essentially along a circumference thereof to define an expandable pocket;

at least partially expanding said cauterization loop from a collapsed configuration to an expanded configuration;

expanding said auxiliary loop from a collapsed configuration to an expanded configuration wherein said auxiliary loop is larger than said cauterization loop and essentially parallel thereto when both loops are in their respective expanded configurations;

at least partially opening said web during said step of expanding;

passing the expanded loops over the selected internal body tissues to be removed, so that said web member substantially surrounds said selected internal body tissues;

partially closing said cauterization loop so that said cauterization loop engages said selected internal body tissues around a base region thereof and so that said auxiliary loop is essentially spaced from said selected internal body tissues while maintaining said web member surrounding said selected internal body tissues so as not to interfere with cutting and cauterization operations;

conducting an electrical current through said cauterization loop to burn through said selected internal body tissues at said base region, thereby severing said selected internal body tissues at said base region; and upon a completed burning of said cauterization loop through said base region, at least partially closing said auxiliary loop, thereby capturing the severed internal body tissues in said web member.

* * * * *